United States Patent [19]

Oommen

[11] Patent Number: 5,293,867
[45] Date of Patent: Mar. 15, 1994

[54] METHOD AND APPARATUS FOR MARKING ELECTRODE LOCATIONS FOR ELECTROENCEPHALOGRAPHIC PROCEDURE

[76] Inventor: Kalarickal J. Oommen, 5459 E. Calle Bosque, Tucson, Ariz. 85718

[21] Appl. No.: 950,271

[22] Filed: Sep. 24, 1992

[51] Int. Cl.⁵ .............................................. A61B 5/00
[52] U.S. Cl. ................................... 128/630; 128/639; 128/898
[58] Field of Search ............... 128/639, 644, 731, 732, 128/733, 735, 898, 907, 630

[56] References Cited

U.S. PATENT DOCUMENTS

| | | | |
|---|---|---|---|
| 3,998,213 | 12/1976 | Price | 128/644 |
| 4,498,480 | 2/1985 | Mortensen | 128/644 |
| 4,537,198 | 8/1985 | Corbett | 128/644 X |
| 4,709,702 | 12/1987 | Sherwin | 128/644 |
| 4,736,751 | 4/1988 | Gevins et al. | 128/732 |
| 4,794,533 | 12/1988 | Cohen | 128/731 X |
| 4,928,696 | 5/1992 | Henderson et al. | 128/644 |

OTHER PUBLICATIONS

Biomedical Electrode Technology Academic Press "Electrode Systems for Recording The EEG In Active Subjects" J. Hanley et al. 1974, pp. 283-313.

Primary Examiner—Lee S. Cohen
Assistant Examiner—Samuel Gilbert
Attorney, Agent, or Firm—Antonio R. Durando; Harry M. Weiss

[57] ABSTRACT

A templet cap that comprises a plurality of elastic straps connected to form a lattice containing all the electrode-positioning locations required to perform an encephalogram according to the International 10/20 System. Each precise electrode-location point along each strap of the cap features a grommet with an eyelet available for marking the scalp of a patient. The cap is positioned with reference to the nasion and inion of the patient in preparation for an EEG. After all points have been identified and marked, the cap is removed and EEG electrodes are attached to the scalp according to normal procedure.

19 Claims, 1 Drawing Sheet

METHOD AND APPARATUS FOR MARKING ELECTRODE LOCATIONS FOR ELECTROENCEPHALOGRAPHIC PROCEDURE

BACKGROUND OF THE INVENTION

1. Field of the Invention

This invention pertains to the general field of electroencephalography. In particular, it provides a new device for marking the scalp of a patient where electrodes are attached to monitor brain activity.

2. Description of the Prior Art

The procedure involved in obtaining an electroencephalograph (EEG) requires that specific points be located on the scalp of a patient for attachment of electrodes by means of a conductive paste for short-term recording and an adhesive (typically collodion) for long-term recording (longer than 24 hours). The specific electrode sites are selected uniformly throughout the world according to the standards specified by the International 10/20 System. Simply stated, this system requires that the distance between the nasion N and the inion I along the top of the scull of a patient (referenced as L1 in FIG. 1 for purposes of illustration) be divided into segments ten, thirty and fifty percent away from the ends, and that each corresponding point be marked on the scalp. Similarly, the distance (L2) passing through the fifty percent point of L1 between the tragus T of each ear is divided into segments corresponding to ten, thirty and fifty percent away from each tragus, and each corresponding point is marked on the scalp. Obviously, the fifty percent point normally corresponds to the point of intersection with L1 and is already marked. Once these positions are established, the two lines (L3 and L4 in FIG. 1) joining the ten-percent points in L1 on both sides of the scalp along the plane containing the four ten-percent points in L1 and L2 are themselves divided into segments corresponding to ten, thirty and fifty percent of each line from the ten-percent points in L1, and each corresponding point is marked on the scalp. Again, the fifty percent points correspond to the points of intersection with L2 and are already marked. Thus, four quadrants become defined between L1, L2, L3 and L4. The midpoint of each of these four quadrants is then found and marked, corresponding to the thirty-percent points of the lines intersecting it, as illustrated in FIG. 1. Thus, a whole lattice of electrode locations with predetermined spacings is found and marked.

A total of 21 electrode locations need to be identified and marked in preparation for an electroencephalograph. This process is obviously time consuming and prone to errors, especially considering the nonideal conditions (asymmetries in the patient's head, the presence of hair, the patient's tendency to move during the procedure) under which these measurements are carried out. Therefore, attempts have been made at simplifying the procedure to shorten the time spent in positioning the electrodes.

U.S. Pat. No. 3,998,213 describes a self-adjustable electrode holder that consists of a cap containing a set of electrodes arranged according to the International 10/20 System. The cap is formed with elastic straps that follow the framework described in FIG. 1, wherein each electrode is attached to the 10/20 System points described above. By using elastic material to manufacture the cap, each strap is able to stretch to conform to different-size heads and retain the 10/20 percent relationship between the electrode locations. Thus, a ready-to-go assembly is provided that only requires good positioning of the cap and connection of the electrode wires to EEG equipment.

The problem with this device is that it can only be used with the set of electrodes incorporated into it. Because of their attachment to the straps in the cap, which are necessarily pushed away from the scalp by the hair of the patient, it is more difficult to maintain electrical contact with the scalp with these electrodes than with standard, free-standing electrodes. In addition, each set of electrodes needs to be washed and sterilized between uses, which is normally accomplished by scrubbing in a detergent medium and, if necessary, a sterilizing chemical. Since the electrodes described in the patent are incorporated into the cap, the entire device must be sterilized, for which the normal procedure is not suitable. The alternative of treating the electrode cap as a disposable unit is obviously too expensive to be considered viable.

Moreover, the cap is usable only for short-term monitoring because of patient's discomfort due to tightness and perspiration induced by the unavoidable temperature rise associated with its use. Poor contact results from this temperature problem, which in turn causes sweat-induced artifacts in the EEG procedure that require frequent adjustments in the equipment's electrical impedance. Thus, the preferred method for long-term monitoring is the application of individual electrodes with collodion, which is not practical using available devices. Therefore, from a practical point of view the cap described in the referenced patent does not fully provide a solution to the problems associated with placing EEG electrodes according to the International 10/20 System. A need remains for a device that simplifies the procedure and that is compatible with utilizing a laboratory's own existing electrodes.

BRIEF SUMMARY OF THE INVENTION

One objective of this invention is a device that enables a user to readily identify and mark electrode placement locations for an EEG on the scalp of a patient according to the International 10/20 System.

Another goal of the invention is a device that is intended for use with the set of electrodes normally provided with conventional EEG electrodes.

Another objective is a device that is compatible with all different kinds of EEG equipment currently in use.

Yet another objective is a device that can be manufactured economically as a disposable item, so as to avoid the need for sterilization between uses.

Finally, a further goal of the invention is the realization of the above mentioned goals in an economical and commercially viable manner, which is achieved by utilizing components that are either already available in the open market or that can be produced at competitive prices.

To the accomplishment of these and other objectives, this invention consists of a templet cap comprising a plurality of elastic straps connected to form a lattice containing all the electrode-positioning locations required to perform an encephalograph according to the International 10/20 System. Each precise electrode-location point along each strap of the cap features a grommet with an eyelet available for marking the scalp of a patient. The cap is positioned with reference to the nasion and inion of the patient in preparation for an EEG. After all points have been identified and marked, the templet cap is removed and EEG electrodes are attached to the scalp according to normal procedure.

Various other purposes and advantages of this invention will become clear from its description in the specification that follows, and from the novel features particularly pointed out in the appended claims. Therefore, to the accomplishment of the objectives described above, this invention consists of the features hereinafter illustrated in the drawings, fully described in the detailed description of the preferred embodiment and particularly pointed out in the claims. However, such drawings and description disclose only one of the various ways in which the invention may be practiced.

DETAILED DESCRIPTION OF THE INVENTION

The main point of this invention concerns the idea of providing a templet for marking the electrode-placement locations according to the International 10/20 System in preparation for a conventional electroencephalogram, so that a much expedited procedure can be effected with standard equipment. The templet consists of a cap having the same electrode-positioning characteristics of the invention disclosed in U.S. Pat. No. 3,998,213, referenced above, but it does not include electrodes for use in combination with the cap. Rather, it provides a multiplicity of guide holes for marking the exact locations for electrode implanting, after which it is removed from the patient's scalp.

Figure 1:
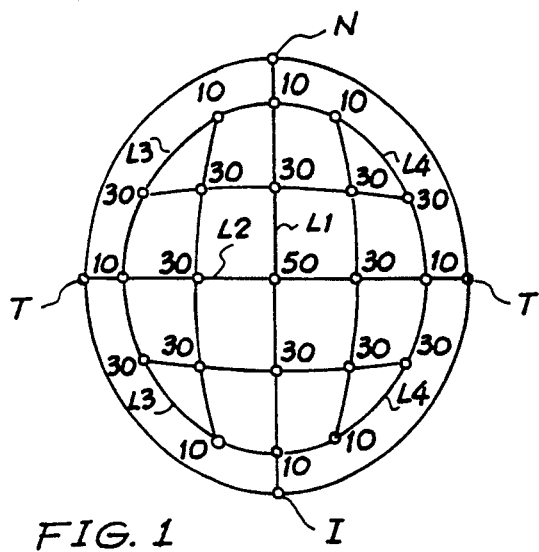
FIG. 1 is a schematic representation of the EEG electrode-placement locations according to the International 10/20 System.
Figure 2:
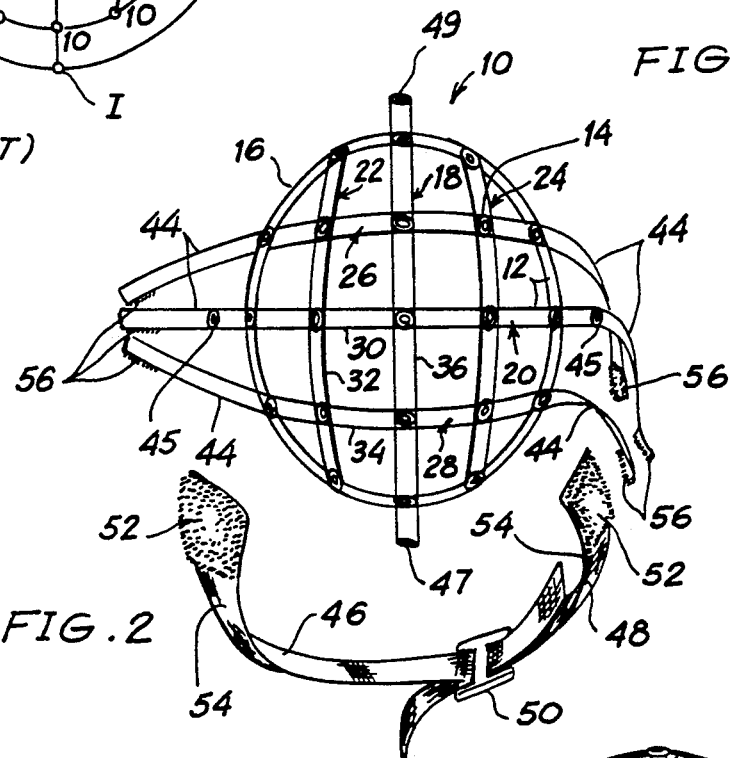
FIG. 2 is a top view of a templet cap according to this invention.

Referring to the drawings, wherein like parts are designated throughout with like numerals and symbols, the preferred embodiment of the templet cap 10 according to this invention is illustrated in FIG. 2. The cap consists of multiple segments of elastic straps 12 joined to form a lattice wherein each point of intersection 14 between pairs of segments corresponds to an electrode-positioning point in the International 10/20 System. In practice, the templet is constructed by combining 7 segments of linear elastic strap material according to the principles outlined above and illustrated in FIG. 1. A first strap 16 forms a circle on the plane containing all ten-percent points; a second, nasion-inion strap 18 connects opposite ends of the circle so formed in the direction between the nasion and the inion and passes through both points; a third, tragus strap 20 connects opposite ends of the circle in the direction between the two tragi; and four quarter straps 22, 24, 26 and 28 divide each of the four quadrants so delineated into four polygons (three quadrilaterals and one triangle) wherein the length of each side of every inner quadrilateral is one quarter the length of the strap segment to which it belongs. For example, looking at the lower-left inner quadrilateral bound by sides 30, 32, 34 and 36 in the figure, side 30 is exactly one quarter the length of strap 20, side 34 one quarter the length of side 28, side 32 one quarter the length of strap 22, and side 36 one quarter the length of strap 18. Thus, the resulting structure necessarily fits the geometry of the International 10/20 System.

Figure 3:
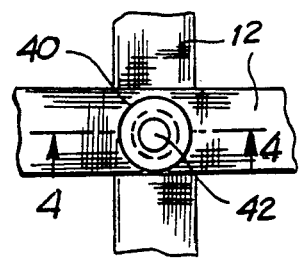
FIG. 3 is a top view of the grommet connection used to fasten the elastic straps of the invention at each point of intersection in a lattice based on the geometry required by the International 10/20 System.
Figure 4:
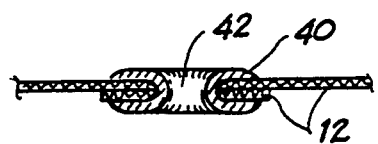
FIG. 4 is a cross-sectional view of the same grommet connection as seen from line 4—4 in FIG. 3, illustrating the clamping action of the grommet over the strap material.

At each point of intersection 14 between two straps a grommet 40 is used to attach the straps 12 to one another, as shown in the partial view of FIG. 3. Each grommet 40 consists of an annular structure having two ends and is formed by passing one end thereof through perforations in the intersecting straps and by compressing both ends to provide a clamp for the strap material. As illustrated in the cross-sectional view of FIG. 4, the grommet thus becomes the fastening means by which the straps are joined at all points of intersection. In addition, an eyelet 42 is provided at the center of each grommet that enables a user to mark its position on the scalp of a patient wearing the templet cap 10. In the preferred embodiment a grommet approximately ⅜ inches in diameter with a ⅛-inch eyelet is used. Because of the cap's lattice structure, the hair of the patient can be parted out of the way and directed through the openings in the lattice to permit direct access to the scalp for accuracy during the marking procedure.

Figure 6:
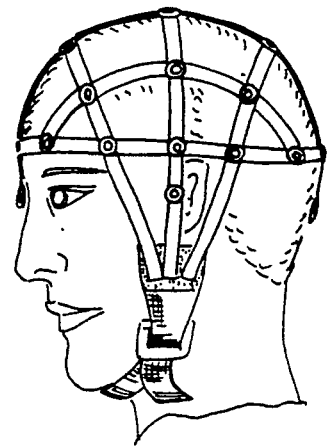
FIG. 6 is a perspective side view of the templet cap of the invention as worn by a patient.

As seen in FIG. 2, the nasion-inion strap 18 is extended to the nasion and inion points and and comprises a nasion marker 47 and an inion marker 49 placed at ten percent of the nasion-inion markers distance from the circular strap 16. Each marker consists of a structure that enables a user to place it precisely on the place to be marked, which could also be a grommet of the type illustrated in FIGS. 3 and 4. The cap 10 also comprises earpiece straps 44 attached to the circular strap 16 (at least one on each side of the cap, but preferably three consisting of extensions of the tragus strap 20 and of the two quarter straps 26 and 28) to provide a structure for aligning the cap with the nasion, inion and tragus reference points in a patient. Tragus markers 45 are placed on the middle earpiece strap in a line collinear with the tragus strap at a distance from the nearest grommet equal to ten percent of the distance between the two tragus markers along that line. Thus, the proper position for the cap may be found by placing each marker 45 over the tragus points in the patient's ears and the nasion-inion markers 47 and 49 over the patient's nasion and inion and adjusting the circular strap 16 so that all of its grommets rest on a substantially horizontal imaginary plane. Two chin straps 46 and 48, slideably and adjustably connected by a buckle 50, are also provided for attachment to each end of the earpiece straps 44 to form a retaining structure under the patient's chin. For that purpose, fastening means, such as fiber-loop components 52 (Velcro ® strips) attached to the end 54 of each chin strap 46 and the ends 56 of the earpiece straps 44 are provided for cooperative engagement below the ears of the patient, as illustrated in FIG. 6. Thus, each earpiece strap may be individually adjusted to ensure the proper positioning of the cap on the head of the patient.

Figure 5:
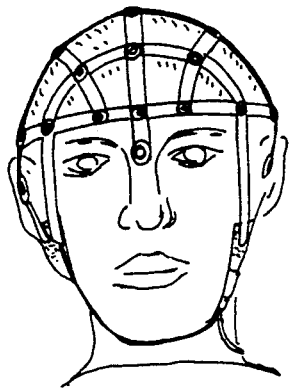
FIG. 5 is a perspective front view of the templet cap of the invention as worn by a patient.

In use, the templet cap 10 of the invention is placed on a patient's head and the markers 45 are placed in front of the tragus of each ear. The circular strap 16 is then adjusted to lie on a plane in such a way that the intersection between the nasion-inion strap and the tragus strap coincides with the midpoint of the distance between the nasion and the inion of the patient. By virtue of the uniform elastic property of all straps, the resulting geometry of the lattice formed by the cap and the position of all grommets will necessarily correspond to the electrode-placement locations prescribed by the International 10/20 System, as illustrated in FIGS. 5 and 6. Thus, each electrode site can be marked by pressing a marker point through the eyelet 42 of each grommet and through the patients hair, which can be easily parted away from the straps toward the open lattice of the cap. Once so marked, the scalp of the patient is ready for application of one electrode to each site according to the procedure required by the particular situation (short-term or long-term). Typically, an individual electrode is attached to each site by using electrode paste or collodion with or without gauze, depending on the degree of permanence required.

It is found that the use of the templet cap of the invention reduces the time of preparation for an EEG procedure from approximately 45 minutes to about 25 minutes. The implantation of each electrode to the scalp of the patient is direct and firm, as in the case following conventional marking procedures; it is not affected by the distortions and lifting that result when the electrodes are attached to the cap. Since the material used for manufacturing the cap is relatively inexpensive (elastic straps and grommets), it can be produced as a disposable item, thus eliminating the need for sterilization between uses. Alternatively, since the cap does not incorporate the electrodes with which it is utilized, it can be washed and sterilized freely according to normal processes without fear of causing damage to electrical components thereof.

Various changes in the details, steps and materials that have been described may be made by those skilled in the art within the principles and scope of the invention herein illustrated and defined in the appended claims. Therefore, while the present invention has been shown and described herein in what is believed to be the most practical and preferred embodiment, it is recognized that departures can be made therefrom within the scope of the invention, which is therefore not to be limited to the details disclosed herein but is to be accorded the full scope of the claims so as to embrace any and all equivalent apparatus and methods.

The embodiments of an invention in which an exclusive property right is claimed are defined as follows:

1. A templet cap for marking electrode positions on a scalp of a patient according to International 10/20 System specifications in preparation for an electroencephalographic procedure, comprising:
   (a) a templet consisting of multiple segments of elastic straps joined to form a lattice wherein each point of intersection between pairs of segments corresponds to an electrode-positioning point according to International 10/20 System specifications;
   (b) a grommet containing eyelet means for determining a position for marking the electrode positions, said grommet joining said each point of intersection between pairs of segments, whereby said straps are attached to one another; and
   (c) two earpiece straps attached to said cap, each strap containing a tragus marker located according to said International 10/20 System specifications.

2. The templet cap described in claim 1, wherein said templet consists of a first strap forming a circle on a plane containing all ten-percent points in a geometry prescribed by said International 10/20 System specifications, a nasion-inion strap connecting opposite points on the circle so formed in a direction between a nasion and an inion in said scalp of a patient, a tragus strap connecting opposite points on said circle in a direction between two tragi along said scalp of a patient, whereby four quadrants are delineated by said nasion-inion strap and said tragus strap, and four quarter straps dividing each of said four quadrants so delineated into four polygons;
   wherein said nasion-inion strap comprises a nasion marker and an inion marker each placed according to said International 10/20 System specifications; and
   wherein the tragus markers on said two earpiece straps are placed in a line collinear with said tragus strap.

3. The templet cap described in claim 1, further comprising two chin straps adjustably connected to one another and attachable to each earpiece strap for fastening under the patient's chin.

4. The templet cap described in claim 3, further comprising fiber-loop components in said chin straps and said earpiece straps for cooperative engagement in forming a retaining structure under the patient's chin.

5. The templet cap described in claim 1, wherein each of said grommets consists of an annular structure having two ends and is formed by passing one end thereof through a perforation in said electrode-positioning point corresponding to each point of intersection between pairs of segments and by compressing both ends to provide a clamp for said straps.

6. The templet cap described in claim 5, wherein each of said grommets is approximately ½ inches in diameter and said eyelet means is about ⅜ inches wide.

7. A method of marking the electrode positions on a scalp of a patient, wherein the patient's hair covers at least a portion of the scalp, according to International 10/20 System specifications in preparation for an electroencephalographic procedure, comprising the following steps:
   (a) providing a templet cap consisting of multiple segments of elastic straps joined to form a lattice wherein each point of intersection between pairs of segments corresponds to an electrode-positioning point according to International 10/20 System specifications; wherein each point of intersection between said multiple segments of straps contains a grommet whereby said straps are attached to one another, each grommet including an eyelet; wherein said templet cap comprises a nasion marker and an inion marker; and wherein two earpiece straps are attached to said templet cap, each earpiece strap containing a tragus marker;
   (b) placing the cap on the patient's scalp and positioning the tragus markers over the tragus of each ear, and placing the nasion marker over the nasion and the inion marker over the inion of the patient;
   (c) parting the patient's hair away from the straps of the cap;
   (d) marking each electrode position on the scalp of the patient by pressing a marker point through the eyelet of each grommet; and
   (e) removing the cap from the head of the patient.

8. The method described in claim 7, wherein the cap provided in said step (a) consists of a first strap forming a circle on a plane containing all ten-percent points in a geometry prescribed by said International 10/20 System specifications, of a nasion-inion strap connecting opposite points on the circle so formed in a direction between a nasion and an inion in said scalp of a patient, of a tragus strap connecting opposite points on said circle in a direction between two tragi along said scalp of a patient, whereby four quadrants are delineated by said nasion-inion strap and said tragus strap, and of four quarter straps dividing each of said four quadrants so delineated into four polygons;

wherein said nasion-inion strap comprises a nasion marker and an inion marker each placed according to said International 10/20 System specifications; and wherein the tragus markers on said two earpiece straps are placed in a line collinear with said tragus strap.

9. The method described in claim 7, further comprising the step of providing two chin straps adjustably connected to one another and attachable to each earpiece strap for fastening under the patient's chin.

10. The method described in claim 9, further comprising the step of providing fiber-loop components in said chin straps and said earpiece straps for cooperative engagement in forming a retaining structure under the pateint's chin, and the step of fastening the fiber-loop components after positioning the tragus markers over the tragus of each ear.

11. The method described in claim 8, wherein said first strap is adjusted after step (b) to lie on a plane in such a way that the intersection between the nasion-inion strap and the tragus strap coincides with a midpoint in a distance between the nasion and the inion along the scalp of the patient.

12. The method described in claim 7, wherein each of said grommets is approximately ½ inches in diameter and said eyelet is about ⅜ inches wide.

13. An apparatus for marking electrode positions on a patient's scalp according to International 10/20 System specifications in preparation for an electroencephalographic procedure, comprising:

(a) a templet cap consisting of multiple segments of elastic straps joined to form a lattice wherein each point of intersection between pairs of segments corresponds to an electrode-positioning point according to International 10/20 System specifications;

(b) means for determining a position for marking said patient's scalp at said each point of intersection between pairs of segments; and (c) two earpiece straps attached to said templet cap, each strap containing a tragus marker located according to said International 10/20 System specifications.

14. The apparatus described in claim 13, wherein said means for determining a position for marking said patient's scalp at said each point of intersection between pairs of segments consists of a grommet joining said pairs of segments at each point of intersection, whereby said straps are attached to one another, each grommet containing an eyelet adapted to receive a marker for marking the patient's scalp therethrough.

15. The apparatus described in claim 14, wherein each of said grommets consists of an annular structure having two ends and is formed by passing one end thereof through a perforation in said electrode-positioning point corresponding to each point of intersection between pairs of segments and by compressing both ends to provide a clamp for said straps.

16. The apparatus described in claim 15, wherein each of said grommets is approximately ½ inches in diameter and said eyelet is about ⅜ inches wide.

17. The apparatus described in claim 13, wherein said templet cap consists of a first strap forming a circle on a plane containing all ten-percent points in a geometry prescribed by said International 10/20 System specifications, a nasion-inion strap connecting opposite points on the circle so formed in a direction between a nasion and an inion in said scalp of a patient, a tragus strap connecting opposite points on said circle in a direction between two tragi in said scalp of a patient, whereby four quadrants are delineated by said nasion-inion strap and said tragus strap, and four quarter straps dividing each of said four quadrants so delineated into four polygons;

wherein said nasion-inion strap comprises a nasion marker and an inion marker each placed according to said International 10/20 System specifications; and wherein the tragus markers on said two earpiece straps are placed in a line collinear with said tragus strap.

18. The apparatus described in claim 13, further comprising two chin straps adjustably connected to one another and attachable to each earpiece strap for fastening under the patient's chin.

19. The templet cap described in claim 18, further comprising fiber-loop components in said chin straps and said earpiece straps for cooperative engagement in forming a retaining structure under the patient's chin.

* * * * *